United States Patent [19]

Rosazza et al.

[11] Patent Number: 5,759,835
[45] Date of Patent: Jun. 2, 1998

[54] BACTERIAL NITRIC OXIDE SYNTHASE

[75] Inventors: John P. Rosazza; Yijun Chen, both of Iowa City, Iowa

[73] Assignee: University of Iowa Research Foundation, Iowa City, Iowa

[21] Appl. No.: 527,113

[22] Filed: Sep. 12, 1995

[51] Int. Cl.$^6$ .................... C12N 9/07; C12N 9/14
[52] U.S. Cl. ............... 435/189; 435/170; 435/111; 435/145
[58] Field of Search .................. 435/195, 872, 435/170, 189, 191

[56] References Cited

U.S. PATENT DOCUMENTS

| | | | |
|---|---|---|---|
| 5,132,407 | 7/1992 | Stuehr et al. | 435/195 |
| 5,268,465 | 12/1993 | Bredf et al. | 435/252.3 |

Primary Examiner—Blaine Lankford
Attorney, Agent, or Firm—Zarley, McKee, Thomte, Voorhees, & Sease

[57] ABSTRACT

Nitric oxide synthase has been discovered to exist in bacteria. The bacterial nitric oxide synthase was purified as much as 1,362-fold by a combination of 2', 5'-ADP-agarose affinity chromatography, and hydroxylapatite chromatography and its unique N-terminal amino acid sequence was identified.

6 Claims, 8 Drawing Sheets

-Thr-Leu-Leu-Asp-Ser-Lys-Ile-Trp-Pro-Asp-Arg-Val-Phe-Ile-Asp-

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

Thr Leu Leu Asp Ser Lys Ile Trp Pro Asp Arg Val Phe Ile Asp
1               5                   10                  15

BACTERIAL NITRIC OXIDE SYNTHASE

BACKGROUND OF THE INVENTION

Nitric oxide synthase (NOS) is an important mammalian enzyme that catalyzes the conversion of L-arginine to L-citrulline and nitric oxide. NOS is an extremely important enzyme in that one of its formed products, nitric oxide (NO) plays a pivotal role in a wide variety of physiological and pathological processes in mammals including vasodilation and regulation of normal vascular tone, inhibition of platelet aggregation, neuronal transmission, cytostasis, hypotension associated with endotoxic shock, inflammatory response-induced tissue injury, mutagenesis, and formation of carcinogenic N-nitrosamines.

NOS has been intensively studied because of its important role in the physiological and pathological functions of mammals. Several isoforms of NOSs from different mammalian tissues and cells have been purified and characterized. Bredt, D. S., et al. (1990) *Proc. Natl. Acad. Sci. U.S.A.* 87, 682–685. The catalytic mechanisms of NOSs have also been broadly studied. Marletta, M. A. (1993) *J. Biol. Chem.* 268, 12231–12234.

Stable isotope studies have shown that NO derives from one of the two equivalent guanidino nitrogens of L-arginine, and that dioxygen is the source of the oxygen atoms incorporated into citrulline and NO. Kwon, N. S., et al. (1990) *J. Biol. Chem.* 265, 13442–13445. Various NOSs have been identified as hemeproteins and flavoproteins. Stuehr, D. J., et al. (1992) *J. Biol. Chem.* 267, 20547–20550; Hevel, J. M., et al. (1991) *J. Biol. Chem.* 266, 22789–22791. Mammalian NOSs have NADPH, FAD, FMN, and calmodulin binding sites as shown by comparison of cDNA and amino acid sequences. Bredt, D. S., et al. (1991) *Nature* 351, 714–718. In addition, $N^G$-hydroxy-L-arginine has been demonstrated to be an oxidative intermediate in the catalytic process. Steur, D. J. et al. (1991) *J. Biol. Chem.* 266, 6259–6263.

Although nitric oxide biosynthesis through oxidative (nitrification) or reductive (denitrification) pathways have been well studied in microorganisms, the formation of nitric oxide from L-arginine by NOS has not yet been reported. It has now been discovered that bacteria present a NOS system. Since it is possible that NO in microorganisms plays a role in mechanisms of infectivity and virulence of infections, the discovery of NOS in microorganisms for the very first time presents a new and unexpected opportunity to exploit possible differences in microbial and mammalian enzymes.

It is therefore a primary objective of the present invention to provide a means of exploiting differences in microbial and mammalian NOSs as a novel intervention method of antibiosis with pathogenic organisms.

It is another primary objective of the present invention to provide a means of isolating NOS from bacteria as a means of studying the differences between microbial and mammalian NOS.

Another objective of the present invention is to isolate NOS from bacteria for the purpose of identifying selective inhibitors of the enzyme.

Yet another objective of the present invention is to isolate and purify the amino acid sequences for bacterial sources of NOS which may be cloned into virus or bacteria for amplification of the gene product.

The method and manner of accomplishing these and other objectives will become apparent from the detailed description of the invention which follows.

SUMMARY OF THE INVENTION

The present invention relates to the occurrence, purification and characterization of the first nitric oxide synthase (NOS) from bacteria. The soluble enzyme has now been purified as much as 1,362-fold by a combination of 2',5'-ADP-agarose affinity chromatography, and hydroxylapatite chromatography. The molecular weight was estimated to be 110.6±0.5 kDa by gel filtration, indicating that the native enzyme exists as a homodimer in solution. A unique fifteen N-terminal amino acid sequence (SEQ ID NO:1) was determined showing it to be different from any known mammalian NOSs.

The discovery of NOS in microorganisms can be used presently to detect similar enzymes in other pathogenic organisms. It also presents new and unexpected opportunities to exploit possible differences in microbial and mammalian enzymes. Further, bacterial NOS enzyme systems may be used as tools in the screening of NOS inhibitors and the identification of selective inhibitors of the enzyme in order to combat and diagnose bacterial infections. As NOS-$_{Noc}$ is an essential metabolic enzyme it is postulated that the presence of this enzyme in *Nocardia* indicates its presence in other bacterial sources as well.

BRIEF DESCRIPTION OF THE DRAWINGS

FIG. 11 is the N-terminal amino acid sequence of bacterial NOS.

DETAILED DESCRIPTION OF THE INVENTION

Figure 1:
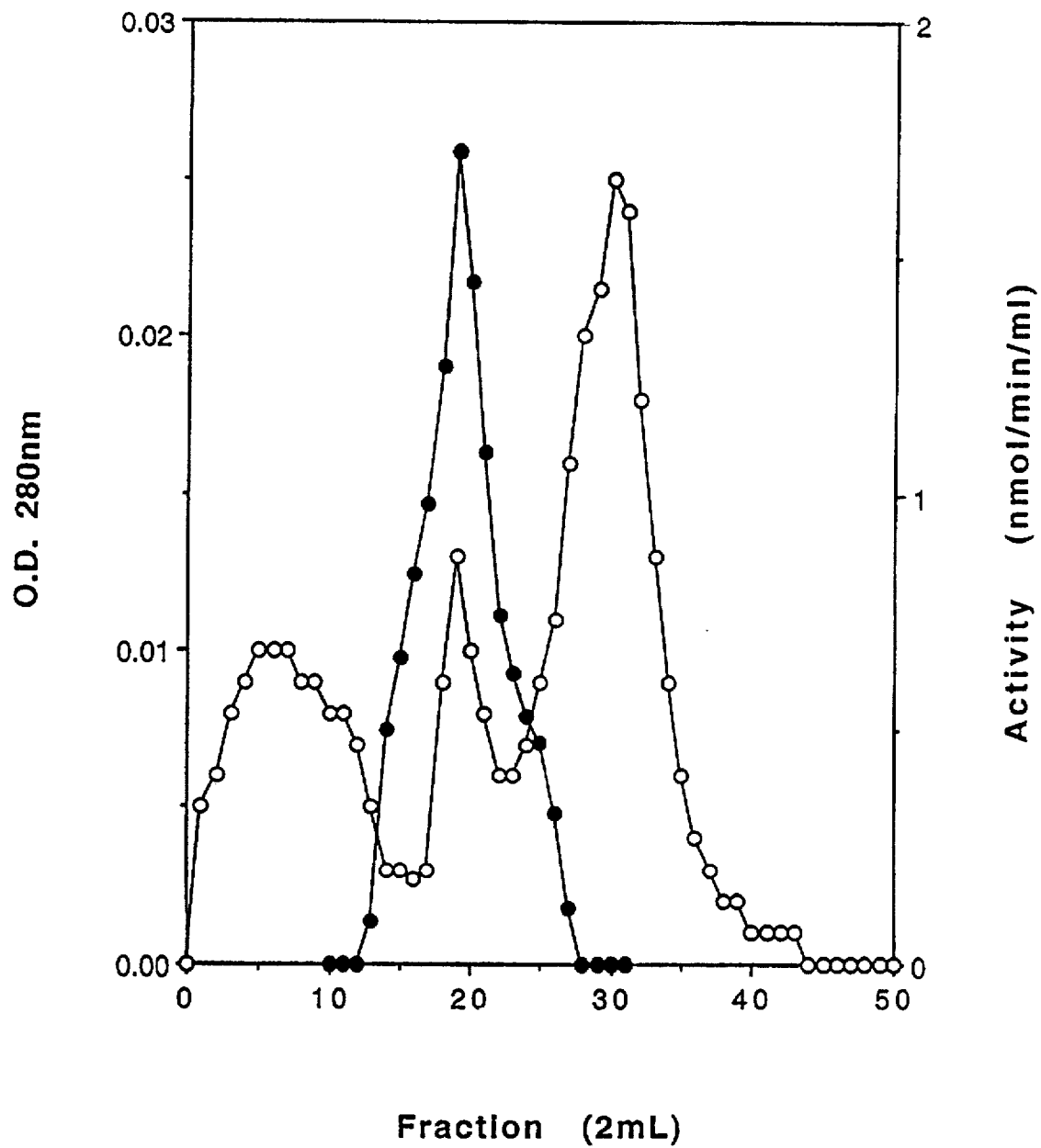
FIG. 1 is the elution profile of $NOS_{Noc}$ with hydroxylapatite chromatography.

The present invention provides a purified and isolated bacterial nitric oxide synthase. Prior to this invention, NOS was known only as a regulator of physiological and pathological processes in mammals and was not known to exist in other types of organisms. This invention demonstrates that NOS exists not only in mammals but in microorganisms.

The discovery of NOS in microorganisms for the first time offers several new opportunities. For example the partial characterization of the amino acid sequence can provide for the ultimate characterization of the gene which encodes it. Briefly, DNA (deoxyribonucleic acid) is a generic term which encompasses an enormous number of complex macromolecules made up of nucleotide units. DNAs consist of four different nucleotides containing the nitrogenous bases adenine, guanine, cytosine, and thymine. A sequential grouping of three such nucleotides (a "codon") codes for one amino acid. A DNA's sequence of codons thus determines the sequence of amino acids assembled during protein synthesis. Since there are 64 possible codons, but only 20 natural amino acids, most amino acids are coded for by more than one codon. This is referred to as the "redundancy" or "degeneracy" of the genetic code.

DNA functions as a blueprint of an organism's genetic information. It is the major component of genes, which are located on chromosomes in the cell nucleus. Only a small part of chromosomal DNA encodes functional proteins.

Messenger ribonucleic acid ("mRNA") is a similar molecule that is made or transcribed from DNA as part of the process of protein synthesis. Complementary DNA ("cDNA") is a complementary copy ("clone") of mRNA made in the laboratory by reverse transcription of mRNA. Like mRNA, cDNA contains only the protein-encoding regions of DNA. Thus, once a cDNA's nucleotide sequence is known, the amino acid sequence of the protein for which it codes may be predicted using the genetic code relationship between codons and amino acids. The reverse is not true, however, due to the degeneracy of the code. Many other DNAs may code for a particular protein.

Collections ("libraries") of DNA and cDNA molecules derived from various species may be constructed in the laboratory or obtained from commercial sources. Complementary DNA libraries contain a mixture of cDNA clones reverse-transcribed from the mRNAs found in a specific tissue source. Complementary DNA libraries are tissue-specific because proteins and their corresponding mRNAs are only made ("expressed") in specific tissues, depending upon the protein. Genomic DNA ("gDNA") libraries, by contrast, theoretically contain all of a species' chromosomal DNA. The molecules present in cDNA and DNA libraries may be of unknown function and chemical structure, and the proteins which they encode may be unknown. However, one may attempt to retrieve molecules of interest from cDNA or gDNA libraries by screening such libraries labeled nucleic acid sequence designed to bond ("hybridize") with a target complementary base sequence. Such "gene cloning" techniques thus exploit the fact that the bases in DNA always hybridize in complementary pairs: adenine bonds with thymine and guanine bonds with cytosine. A gene probe for potentially isolating DNA or cDNA encoding a protein may be designed once the protein's amino acid sequence, or a portion thereof, is known.

Thus, by isolating and determining the N-terminal amino acid sequence of bacterial NOS, the inventors have provided a means for those of ordinary skill in the art to utilize a gene probe to isolate the nucleotide sequence of bacterial NOS to clone and reproduce the enzyme. The purification of this enzyme presents a new and unexpected opportunity to exploit possible differences in microbial and mammalian enzymes. The purification and sequence of human NOS is disclosed in U.S. Pat. No. 5,268,465 to David Bredt which is incorporated herein by reference. The bacterial NOS can be used in standard in vitro assays to compare its properties to those of human NOS to identify differences which may be exploited. These types of assays are common to those of skill in the art. One typical assay is disclosed herein. Thirdly, bacterial NOS enzyme systems can be used as tools in the screening of NOS inhibitors, a class of new drugs that is being developed world-wide. The microbial NOS affords a screening target that permits the identification of "selective inhibitors" of the enzyme. An NOS inhibitor that is selective for microbial NOS is useful as a new avenue for combating infection and infectious diseases. Its in vivo activity can also be used in comparison with human NOS to identify those compounds which specifically target bacterial NOS. Also, the enzyme systems may be useful in diagnosing infections caused by NOS-containing microorganisms.

The N-terminal sequence of bacterial NOS has now been determined to consist of:

NH$_2$-Thr-Leu-Leu-Asp-Ser-Lys-Ile-Trp-Pro-Asp-Arg-Val-Phe-Ile-Asp-   SEQ ID NO: 1

Availability of the bacterial NOS N-terminal amino acid sequence permits the production of mutant forms of the present NOS enzyme via mutagenesis of the gene. Mutant forms of the NOS gene may be useful to produce microorganisms such as new strains of bacteria, which overproduce nitric oxide at higher levels, or under even more stringent environmental conditions.

*Nocardia* species produces a 100,000×g soluble form of nitric oxide synthase that has been designated NOS$_{Noc}$. Previously, the partially purified enzyme was used to confirm its catalytic nature, and to permit preliminary determinations of substrates, products, and cofactors required in the ocnversion of L-arginine to L-citrulline and NO. Chen, Y. and Rosazza, J. P. (1994) *Biochem. Biophys. Res. Commun.* 203, pp. 1251–1258. Preliminary evidence demonstrated that NOS$_{Noc}$ enzyme activity was dependent upon the presence of NADPH, Ca++, FAD, FMN, and H$_4$B thus demonstrating the similarity of the *Nocardia* enzyme with NOS from polymorphonuclear neutrophils. Omission of any of these cofactors from incubation mixtures results in loss of all enzyme activity.

Figure 2:
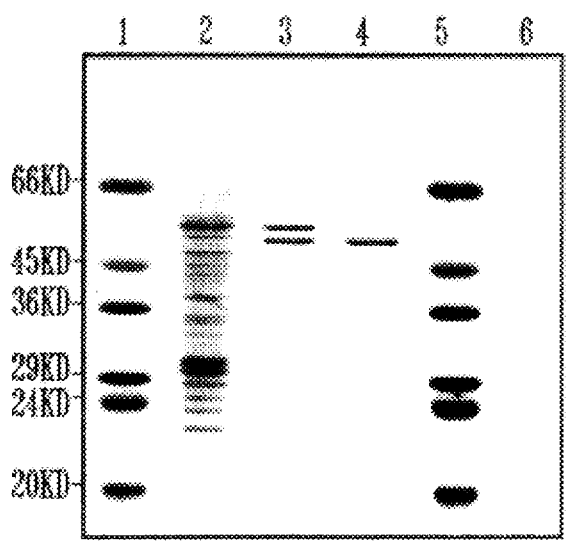
FIG. 2 is SDS-polyacrylamide gel electrophoresis of $NOS_{Noc}$.

The NOS$_{Noc}$ enzyme is estimated to possess a mass of 110.6$^±$0.5 kDa. The denatured molecular weight of the enzyme is estimated to be 51,900 (FIG. 2). Thus, NOS$_{Noc}$ appears to be a homodimeric protein.

NOS$_{Noc}$ is colorless and has an absorption maximum which was observed at 280 nm in the UV/Vis spectrum. As previously shown, fifteen amino acid residues from the N-terminal end of the protein have been identically determined by Edman degradation in duplicate analysis of two separately purified NOS$_{Noc}$ samples.

Figure 3:
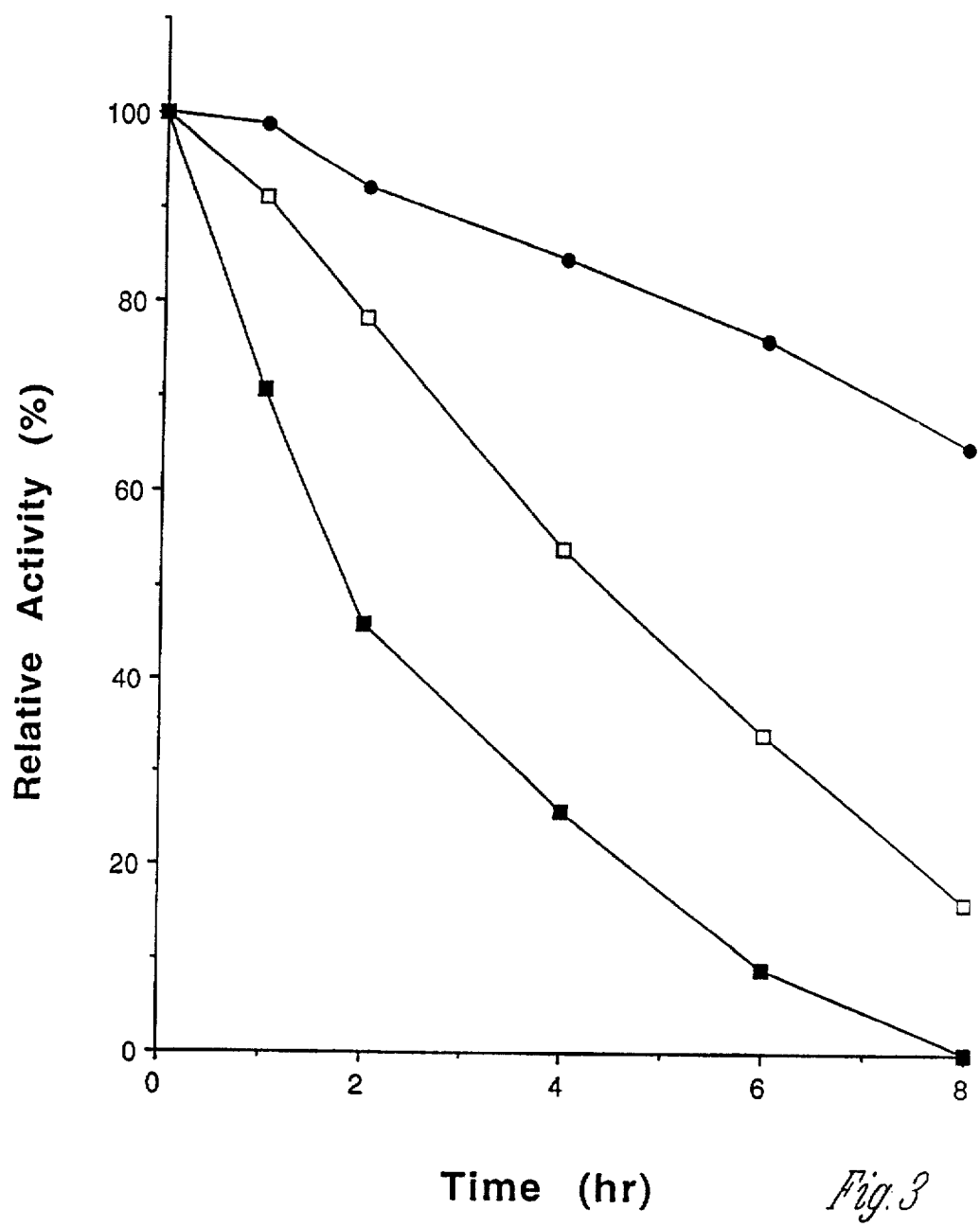
FIG. 3 is a linear regression plot of the activity of $NOS_{Noc}$ at 4° C., 25° C., and 37° C.
Figure 4:
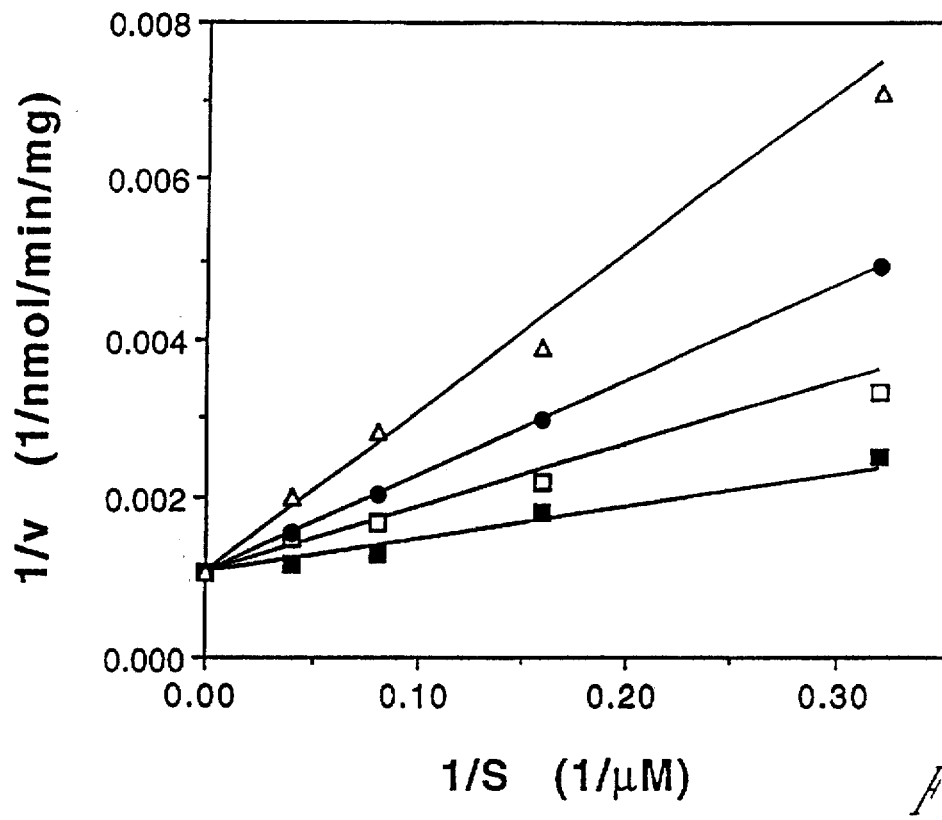
FIG. 4 is a double reciprocal plot of the inhibition of $NOS_{Noc}$ by $N^G$-methyl-L-arginine in the presence of L-arginine. Closed squares, 0 µM L-NMA; open squares, 12.5 µM L-NMA; closed circles, 25 µM L-NMA; open triangles, 50 µM L-NMA. The values are the mean of three measurements.
Figure 5:
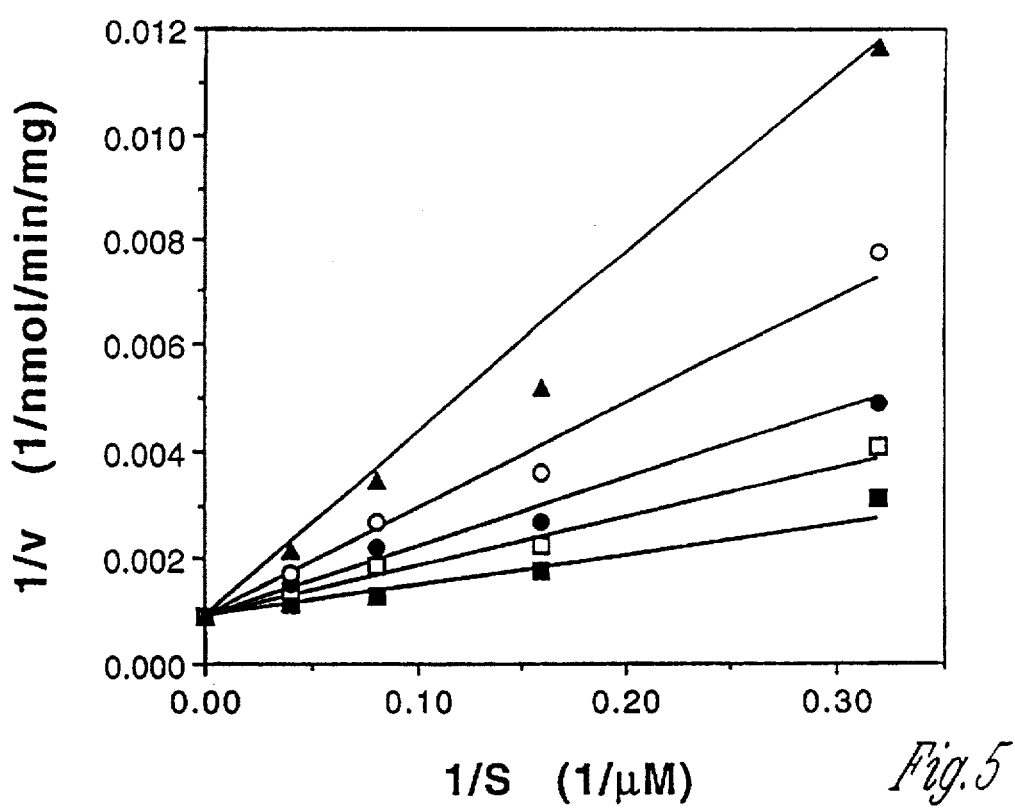
FIG. 5 is a double reciprocal plot of the inhibition of $NOS_{Noc}$ by $N^G$-nitro-L-arginine in the presence of L-arginine. Closed squares, 0 µM L-NNA; open squares, 6.125 µM L-NNA; closed circles, 12.5 µM L-NNA; open circles, 25 µM L-NNA; closed triangles, 50 µM L-NNA. The values are the mean of three measurements.
Figure 6:
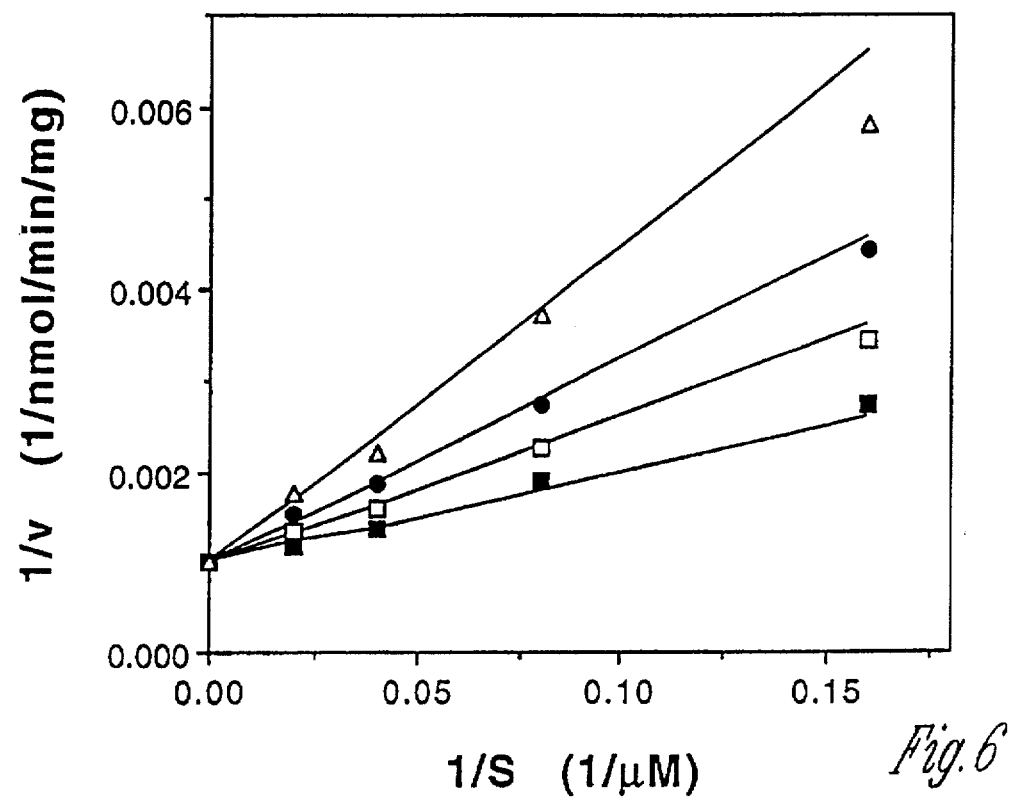
FIG. 6 is a double reciprocal plot of the inhibition of $NOS_{Noc}$ by $N^G$-methyl-L-arginine in the presence of $N^G$-hydroxy-L-arginine. Closed squares, 0 µM L-NMA; open squares, 12.5 µM L-NMA; closed circles, 25 µM L-NMA; open triangles, 50 µM L-NMA. The values are the mean of three measurements.
Figure 7:
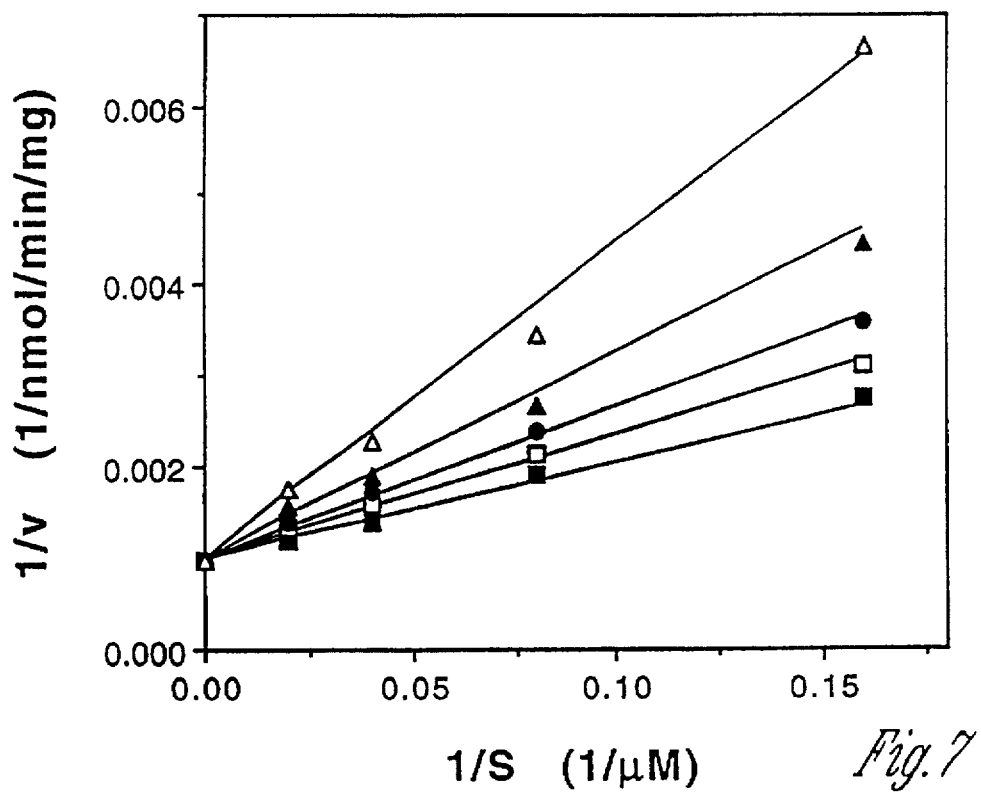
FIG. 7 is a double reciprocal plot of the inhibition of $NOS_{Noc}$ by $N^G$-nitro-L-arginine in the presence of $N^G$-hydroxy-L-arginine. Closed squares, 0 µM L-NNA; open squares, 6.125 µM L-NNA; closed circles, 12.5 µM L-NNA; open circles, 25 µM L-NNA; closed triangles, 50 µM L-NNA. The values are the mean of three measurements.
Figure 8:
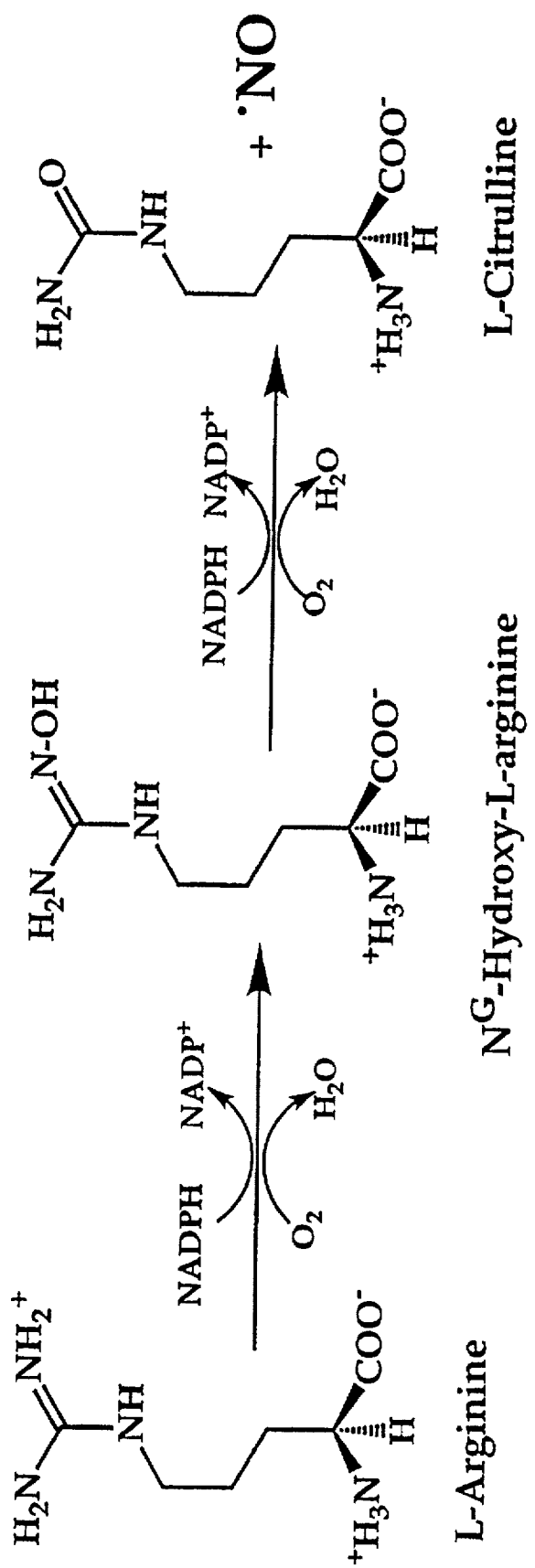
FIG. 8 is the biosynthetic pathway of nitric oxide from L-arginine by $NOS_{Noc}$.
Figure 9:
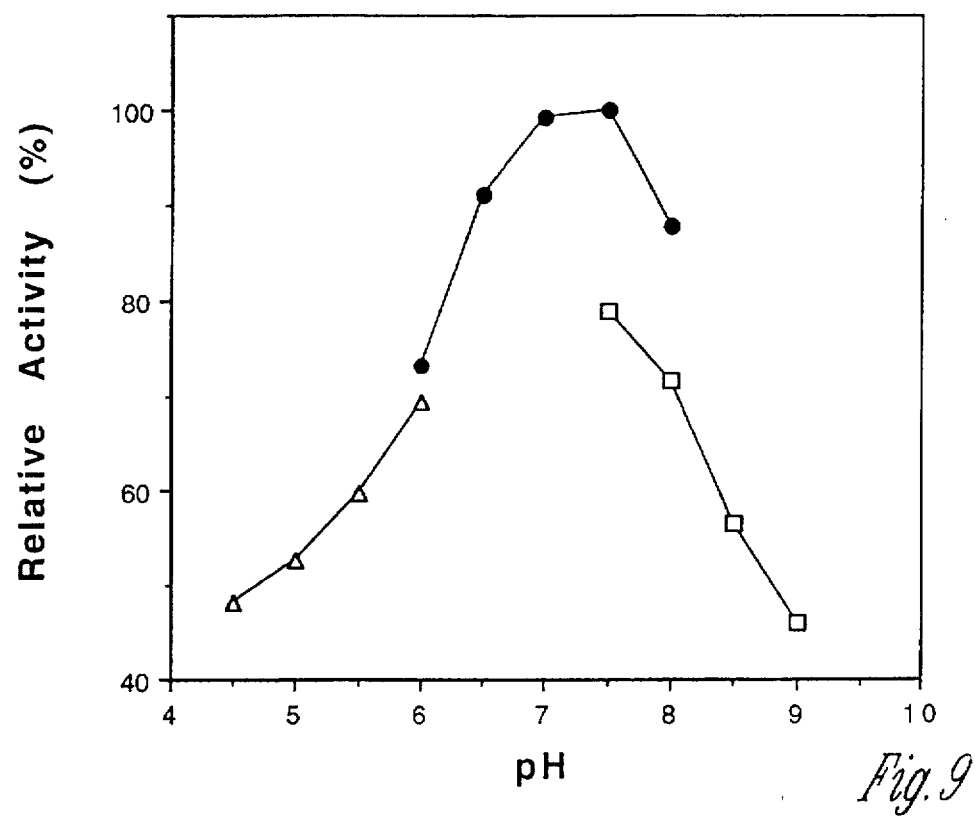
FIG. 9 is the effect of pH on $NOS_{Noc}$ activity. Open triangles, 50 mM sodium acetate buffer; closed circles, 50 mM potassium phosphate buffer; open squares, 50 mM Tris-HCl buffer. The data are representative of three determinations.
Figure 10:
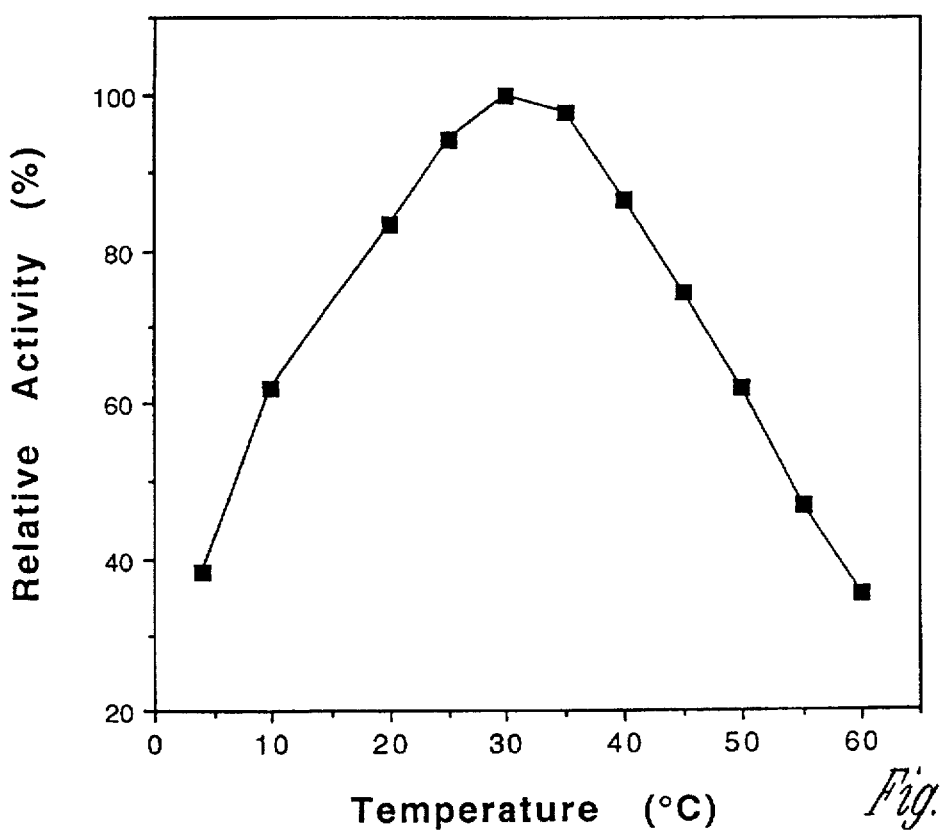
FIG. 10 is the effect of temperature on $NOS_{Noc}$ activity. The values are the mean of three measurements.

The stability of NOS$_{Noc}$ was measured at 4° C., 25° C., and 37° C. The enzyme lost about 30% of its activity after 8 hours at 4° C., whereas it exhibited half-lives of 4 h and 2 h at 25° C. and 37° C., respectively (FIG. 3).

The optimum pH of NOS$_{Noc}$ occurs between 7.0 and 7.5 with potassium phosphate buffer, and enzyme activity is maximum at 30° C.

The purification of this enzyme also presents a method for assaying for the presence of bacterial species in body fluids by developing monoclonal or polyclonal antibodies which recognize an antigenic site from the unique N-terminal region.

Antibody preparations are made according to techniques which are well known in the art. Both polyclonal and monoclonal antibodies are contemplated, production of both of which are well known. According to one method for obtaining a polyclonal antibody preparation, rabbits are immunized with a purified preparation of calmodulin-dependent NOS, as described above. The antiserum will preferably be affinity-purified by incubation with purified NOS and elution with 4M MgCl in 200 mM Tris-HCl buffer (pH 7.4). The eluate will desirably be dialyzed against phosphate buffered saline with 0.1% Triton X100.

Antibodies can be used for immunohistochemical localization of bacterial NOS, or for quantitative assays on biological fluids or samples, such as in an enzyme-linked immunoadsorbent assay or radioimmunoassay. Such assays can determine the presence of bacteria which express this NOS enzyme either in simply which other microorganisms express this enzyme.

The invention will be further described by reference to the following detailed example.

EXAMPLE

L-[2,3-$^3$H]Arginine (53 Ci/mmol; 1 Ci=37 GBq) was purchased from DuPont/NEN (Boston, Mass.). (6R)-5,6,7,8-Tetrahydrobiopterin ($H_4B$) was obtained from Biochemical Research Inc. (Natick, Mass.). Hydroxylapatite was from Bio-Rad (Hercules, Calif.). $N^G$-Hydroxy-L-arginine (L-NOHA) was from Alexes Corp. (San Diego, Calif.). L-Arginine, $N^G$-methyl-L-arginine (L-NMA), $N^G$-nitro-L-arginine (L-NNA), 2',5'-ADP-agarose and other reagents were purchased from Sigma Co. (St. Louis, Mo.).

*Nocardia* species (YC-122540; NRRL 5646) is kept in the University of Iowa, College of Pharmacy culture collection and is grown and maintained on slants of Sabouraud-dextrose agar or sporulation agar (ATCC #5 medium). In this experiment, shaken flask cultures were grown by a standard two-stage fermentation protocol in 200 ml of sterile soybean meal-glucose medium held in stainless steel-capped 1-L DeLong culture flasks. Betts, R. E. et al. (1974) *J. Med. Chem.* 17, pp. 599–602. The medium contained (w/v) 2% glucose, 0.5% yeast extract, 0.5% soybean meal, 0.5% NaCl, and 0.5% $K_2HPO_4$ in distilled water and was adjusted to pH 7.0 with 6N HCl and then autoclaved at 121° C. for 20 minutes. Cultures were incubated with shaking at 250 rpm at 28° C. on New Brunswick Scientific G25 Gyrotory shakers. A 10% inoculum derived from 72 h-old stage I cultures was used to initiate stage II cultures which were incubated as before. Stage II cultures were harvested after 48-h, filtered through cheesecloth and centrifuged at 8,000×g for 10 min. Typical wet weight cell yields by this cultivation process are approximately 25 gm/L.

For preparation of crude cell free extracts, 5 g (wet weight) of the resulting cell paste was suspended in 20 ml of cold 10 mM Tris-HCl buffer (pH 7.5) containing 1 mM DTT, 1 mM EDTA and 2 μM $H_4B$, and disrupted for 5 minutes over ice with a Sonifier Cell Disrupter 350 (Branson Sonic Power Co., CT). Cell debris was removed by centrifugation at 100,000×g for 60 minutes at 4° C. in a Beckmann L8-55 ultracentrifuge. The 100,000×g supernatant was used directly for subsequent enzyme purification steps which were conducted at 4° C.

$NOS_{Noc}$ activity was determined spectophotometrically based on the rapid and quantitative oxidation of oxyhemoglobin (oxyHb) to methemoglobin by NO (36,37). Assays for NOS activity were carried out using a Shimadzu 160 spectrophotometer by observing the increase in absorbance at 401 nm at 25° C. A typical sample assay contained 50 mM potassium phosphate buffer (pH 7.5), 4 μM oxyHb, 100 μM L-arginine of L-NOHA (for kinetic experiments), 100 μM NADPH, 1 mM $CaCl_2$, 10 μM FAD, 10 μM FMN, 80 μM $H_4B$, 150 μM DTT and 0.1–2 μg enzyme in a final volume of 1 ml. For assays, the reference cuvette contained all components except for L-arginine or L-NOHA. All assays were initiated by adding enzyme. $NOS_{Noc}$ activity is expressed as nitric oxide produced in nmole/min/mg protein.

NOS activity was also determined by measuring the decrease in absorbance at 340 nm as NADPH was consumed during the conversation of L-arginine to L-citrulline by NOS. Furfine, E. S., et al. (1993) *Biochemistry* 32, pp. 8512–8517. For the NADPH assay, one unit of $NOS_{Noc}$ activity is defined as the amount of enzyme oxidizing 1 μmol of NADPH per minute at 25° C.

Crude 100,000×g supernatants (15–20 ml, 80–90 mg protein) were applied to 4-ml 2',5'-ADP-agarose columns equilibrated with 10 mM Tris-HCl buffer (pH 7.5) containing 1 mM DTT, 1 mM EDTA and 2 μM $H_4B$. Columns were subsequently washed with 20 ml of buffer, 120 ml of buffer containing 0.5M NaCl, 20 ml of buffer containing 0.5 mM NADH, 20 ml of buffer containing 0.5 mM NADP$^+$, and 20 ml of buffer. Enzyme activity was then eluted with 10 ml of buffer containing 10 mn NADPH. The enzyme active fraction was concentrated with an Amicon concentrator (PM-10 membrane) and washed with additional buffer to remove residual NADPH, and finally concentrated to approximately 1 ml before being applied to a 5-ml hydroxylapatite column (1.5×8 cm) equilibrated with 10 mM potassium phosphate buffer (pH 7.0) containing 1 mM DTT. The hydroxylapatite column was subsequently washed with 50 ml of the same buffer. The enzyme was then eluted with 100 ml of phosphate buffer using a linear gradient (10–100 mM) while 2 ml fractions were collected. The fraction (6 ml) corresponding to the three center fractions containing the enzyme was combined and concentrated to approximately 0.2 ml for subsequent analysis.

Citrulline produced by $NOS_{Noc}$ was determined by monitoring the formation of $^3$H-citrulline from $^3$H-arginine. Bredt, D. S., and Snyder, S. H. (1989) *Proc. Natl. Acad. Sci. U.S.A.* 86, pp. 9030–9033. Reaction samples (50 μl, 100 μM arginine and 1 μCi radioactivity) in 2 ml of stop buffer (20 mM HEPES and 2 mM EDTA, pH 5.5) were applied to a fresh 1-ml Dowex AG50W-X8 (Na+ form, 100–200 mesh) column. Labeled citrulline was eluted with 2 ml of distilled water, and the eluates were collected. Aliquots of 0.1 ml of eluate were dissolved in 5 ml of Budget Solve cocktail in 10 ml scintillation vials, and radioactivity was measured in a Beckman LS 3801 liquid scintillation system.

Nitrite was measured spectrophotometrically using Griess reagent. Green, L. C., et al. (1982) *Anal. Biochem.* 126, pp. 131–138. Griess reagent (0.5 ml of a solution of 1% sulfanilamide and 0.1% naphthylethylenediamine in 2% phosphoric acid) was added to 0.5 ml of $NOS_{Noc}$ reaction mixtures. After standing for 15–30 minutes at room temperature, the absorbance at 540 nm was measured. Nitrite concentrations were estimated by comparison with a standard curve at the range of 0–1.0 μg/ml prepared with standard sodium nitrite in water.

Oxygen consumption during $NOS_{Noc}$ incubations was measured with a YSI Model 53 Oxygen Monitor equipped with a 3 ml water-jacketed reaction vessel kept at 25° C.

Oxygen concentrations were calculated based on the deflection of the chart recorder versus 206 μM oxygen-total oxygen content in the reaction vessel. Koppenol, W. H. (1985) *Adv. Free Radical Biol. Med.* 1, 91–131.

Electrophoresis was performed using a Bio-Rad Mini-PROTEIN II dual slab cell with a discontinuous buffer system, and 12% separating gel. Laemmli, U. K. (1970) *Nature* 227, pp. 680–685. Gels were stained with Coomassie blue.

Analytical gel filtration chromatography was carried out using an Alltech Macrosphere 150 column (7μ, 4.6×25 cm). The mobile phase of 10 mM Tris-HCl buffer (pH 7.5) containing 1 mM DTT and 0.2M NaCl, was used to equilibrate the column and to elute protein samples at a flow rate of 0.5 ml/min. Eluting protein peaks (retention volumes, $R_v$) were monitored at 280 nm. Standard proteins ($M_r$) used were bovine thyroglobulin (669,000, $R_v$ 1.82 ml), horse spleen apoferritin (433,000, $R_v$ 1.97 ml), sweet potato β-amylase (200,000, $R_v$ 2.27 ml), yeast alcohol dehydrogenase (150,000, $R_v$ 2.47 ml), bovine serum albumin (66,000, $R_v$ 2.76 ml), and bovine carbonic anhydrase (29,000, $R_v$ 3.16 ml).

Purified $NOS_{Noc}$ (6 μg protein) was centrifuged onto a Prospin membrane until dry to remove phosphate salts and DTT. The protein on the membrane was washed and removed with 1 ml of methanol-water (1:1), and the N-terminal amino acid sequence was determined by automated microsequencing with Edman degradation reactions on a 475A Sequencer (Applied Biosystems, Inc.) performed in the Protein Structure Facility at the University of Iowa, Iowa City, Iowa. The N-terminal amino acid sequence was determined twice, using separately purified samples of $NOS_{Noc}$.

Purified $NOS_{Noc}$ (Table I) was used in the determination of enzyme activity vs. incubation temperature, pH, and enzyme stability. For temperature optimum experiments, the buffer was pH 7.5, 50 mM potassium phosphate. The samples were incubated at various temperatures for 5 minutes before each determination. For pH optimum determinations, three different buffers were employed over appropriate pH ranges. These included 50 mM sodium acetate, 50 mM potassium phosphate, and 50 mM Tris-HCl.

Enzyme stability experiments were conducted by incubating $NOS_{Noc}$ in pH 7.5, 50 mM potassium phosphate buffers held at 4°, 25° or 37° C. For these experiments, each determination was estimated in triplicate.

TABLE I

Purification of $NOS_{Noc}$*

| | Crude extract | ADP-agarose | Hydroxylapatite |
|---|---|---|---|
| Total protein (μg) | 82,720 | 348 | 24 |
| Total activity (nmol/min) | 12.31 | 10.92 | 4.83 |
| Specific activity (nmol/min/mg protein) | 0.149 | 31.34 | 202.86 |
| Yield (%) | 100 | 88.7 | 39.2 |
| Purification factor (fold) | 0 | 210 | 1362 |

*The data are representative of two experiments.

Concentrations of protein in all purification steps were measured by the Bradford protein microassay using bovine serum albumin as standard. Bradford, M. M. (1976) *Anal. Biochem.* 72, pp. 248–252. The UV-visible absorption spectrum of $NOS_{Noc}$ (10 μg in 100 μl of pH 7.0, 20 mM phosphate buffer) was determined using a SIM-AMINCO Model DW2000 UV-Visible spectrophotometer with 100 μl cuvettes. The spectrum was scanned over the range of 200–600 nm.

The results of purification of *Nocardia* $NOS_{Noc}$ are summarized in Table I. $NOS_{Noc}$ was purified 1,362-fold with two chromatographic steps. The first step of purification involved affinity chromatography over 2',5'-ADP-agarose to which the enzyme binds. Although most of the protein in crude extracts passed through the column, $NOS_{Noc}$ was bound to the affinity matrix. After a series of washes with NaCl, NADH and NADP+, enzyme activity was selectively eluted from the column with 10 mM NADPH. Lower concentrations of NADPH resulted only in the partial elution of $NOS_{Noc}$ from 2',5'-ADP-agarose and substantial peak-broadening. Although $NOS_{Noc}$ was purified some 210-fold by this step, a number of contaminating proteins were also eluted from the column by 10 mM NADPH. Final purification of $NOS_{Noc}$ was achieved by hydroxylapatite chromatography. The elution profile of $NOS_{Noc}$ activity and other proteins from the hydrosylapatite column are shown in FIG. 1. There were three major protein peaks observed in the elution profile. The relativity small protein peak in the middle of the chromatogram corresponded to $NOS_{Noc}$ enzyme activity. $NOS_{Noc}$ activity from the hydroxylapatite column was eluted in 16 fractions (32 ml) with 40–50 mM phosphate buffer. The three fractions (6 ml) in the center of the enzyme activity peak were combined and concentrated to approximately 0.2 ml. The enzyme was determined to be greater than 98% pure by SDS-PAGE gel electrophoresis (FIG. 2).

Purified $NOS_{Noc}$ had a specific activity of 202.9 nmole of NO per mg of protein per minute. This represented a 1,362-fold purification of $NOS_{Noc}$ from crude extracts with a 39.2% recovery of total enzyme activity. Based on this purification, soluble NOS represents approximately 0.03% of the crude supernatant proteins of the microorganism.

Based upon comparison of $NOS_{Noc}$ Rv of 2.48 ml vs. the $R_v$ of proteins of known molecular weights by Macrosphere 150 gel filtration chromatography, the purified enzyme was estimated to possess a mass of 110.6±0.5 kDa. By SDS-PAGE, the denatured molecular weight of the enzyme was estimated to be 51,900 (FIG. 2). Thus, $NOS_{Noc}$ appears to be a homodimeric protein.

$NOS_{Noc}$ is colorless, and an absorption maximum was observed at 280 nm in the UV/Vis spectrum. A shoulder at 390–430 nm which corresponds to the characteristics of a hemeprotein, was barely evident in the UV-visible spectrum. Absorption in the range of 450–550 nm, typical for flavins, was not observed. Fifeen amino acid residues from the N-terminal end of the protein were identically determined by Edman degradation in duplicate analyses of two separately purified $NOS_{Noc}$ samples. The $NOS_{Noc}$ has the N-terminal amino acid sequence of SEQ ID NO:1 (FIG. 11). The BLASTP and TBLASTN programs were employed to search updated SwissProt, GenPept, GenBank, and EMBL databases to demonstrate no matching amino acid sequences. Altschul, S. F., et al. (1990) *J. Mol. Biol.* 215, pp. 403–410.

It should be appreciated that the *Nocardia* species utilized in the above example is representative of all *Nocardia* species and, presumably, all bacterial species since bacterial species present the same essential metabolic functions, thus producing the same NOS enzyme which has been isolated and purified in the present invention.

Stoichiometric determinations of oxygen consumed, NADPH oxidized, NO and citrulline formed, and kinetic experiments were carried out to confirm that L-NOHA is an intermediate in the biosynthesis of nitric oxide from L-arginine. Table II shows the stoichiometric relationships between product formation and cofactor utilization with either L-arginine or L-NOHA as substrate. With L-arginine as substrate, $NOS_{Noc}$ consumed two mole equivalents each of NADPH and $O_2$ while 1 mole each of L-citrulline and nitrite were formed. With L-NOHA as substrate, $NOS_{Noc}$ consumed one mole equivalent each of NADPH and $O_2$ while 1 mole each of L-citrulline and nitrite were formed.

TABLE II

Stoichiometry of L-arginine and NG-hydroxy-L-arginine as substrates for $NOS_{Noc}$[a]

| Substrate | Citrulline formation (nmole) | Nitrile formation (nmole) | NADPH consump (nmole) | Oxygen consump (nmole) |
|---|---|---|---|---|
| L-Arginine | 4.21 ± 0.17 | 4.63 ± 0.28 | 8.77 ± 0.32 | 8.89 ± 0.33 |
| NG-Hydroxy-L-arginine | 4.54 ± 0.21 | 4.57 ± 0.20 | 4.38 ± 0.24 | 4.46 ± 0.16 |

The comparison between L-NOHA and L-arginine as a substrate for $NOS_{Noc}$ was made. The Km value measured for L-NOPHA was nearly 3-fold greater (15.8 μM) than that measured for L-arginine (5.7 μM). $V_{max}$ values determined for L-NOHA and L-arginine at 549 vs 607 nmol/min/mg protein, respectively, were similar. By fitting the experimental data to the EZ-FIT program developed by Perrella, NO synthesis from either L-NOHA or L-arginine was competitively inhibited by $N^G$-methyl-and $N^G$-nitro-L-arginine. Perrella, F. W. (1988) Anal. Biochem. 174, pp. 437–447. However, the inhibition constants (Ki) of different inhibitors for different substrates were not the same. The Ki of L-NMA for L-NOHA was 0.6 times higher than that for L-arginine, while Ki of L-NNA for L-NOHA was approximately 1.2-fold greater than that for L-arginine (Table III). Both L-NMA and L-NNA show typical competitive inhibition for both L-NOHA and L-arginine (FIGS. 4–7).

TABLE III

Kinetic properties of $NOS_{Noc}$[a]

| Kinetic constant[b] | L-Arginine | $N^G$-Hydroxy-L-arginine |
|---|---|---|
| Km(μM) | 5.7 ± 0.3 | 15.8 ± 0.8 |
| Vmax(nmole/min/mg protein) | 274 ± 13 | 303 ± 15 |
| Ki of $N^G$-methyl-L-arginine | 6.2 ± 0.4 | 21.4 ± 1.2 |
| Ki of $N^G$-nitro-L-arginine | 9.8 ± 0.6 | 21.4 ± 1.2 |

[a]The data are the mean S.D. of three determinations
[b]The kinetic constants were obtained by fitting experimental data to EZ-FIT program. The values of Ki were obtained by fitting to the model of competitive inhibition.

In the present invention, $NOS_{Noc}$ was purified using a combination of 2',5'-ADP agarose and hydroxylapatite column chromatographic steps resulting in a 1,362-fold purification of the enzyme, and 39.2% recovery of total enzyme activity originally found in crude 100,000×g supernatants. Column affinity chromatography over 2',5-ADP-agarose has been used in the purification of every reported mammalian NOS obtained from various tissues and cells. See for e.g. Bredt, D. S. and Snyder, S. H. (1990) Proc. Natl. Acad. Sci. U.S.A. 87, pp. 682–685. Experimental results demonstrate that $NOS_{Noc}$ was tightly bound to 2,5-ADP-agarose and, after several prewashes, was best eluted with 10 mM NADPH to yield maximum activity. Anion exchange and/or gel filtration chromatography have also been widely used in mammalian NOS purifications. However, hydroxylapatite chromatography was more successfully used as a final step for subsequent purification of $NOS_{Noc}$.

By SDS-polyacrylamide gel electrophoresis, the purified protein ran as a prominent major band indicating a molecular weight of 51.9 kDa, considerably smaller than mammalian NOSs which give denatured molecular weights by SDS-PAGE in the range of 115–150 kDa. Different types of mammalian NOSs have been characterized as hemeproteins. Stuehr, D. J., and Ikeda-Sait., M. (1992) J. Biol. Chem. 267, pp. 20547–20550. Limitations in the amount of pure enzyme precluded conclusive UV/Vis spectral analysis of $NOS_{Noc}$. However, the appearance of a shoulder at 390–430 nm suggests the presence of heme in the Nocardia enzyme, while lack of absorption in the range of 450–550 nm suggests that FAD and FMN are not bound to the purified enzyme. The fifteen amino acid N-terminal sequence screened through the BLAST database was unlike sequences reported for purified mammalian NOSs. $NOS_{Noc}$ displays reasonable stability vs. mammalian NOSs. $NOS_{Noc}$ loses nearly 30% of its activity after 8 h at 4° C., wheareas the half lives of most mammalian NOSs under similiar conditions are less than 6 h.

$N^G$-Hydroxy-L-arginine is a demonstrated intermediate in the biosynthesis of nitric oxide from L-arginine in mammalian tissues and cells. Stuehr, D. J., et al. (1991) J. Biol. Chem. 266, pp. 6259–6263. In examining the intermediacy of L-NOHA in the synthesis of NO by $NOS_{Noc}$, the results demonstrated that the Km of 15.8 mM for L-NOHA is about 3-fold greater than that for L-arginine. This result is similar to that reported for macrophage NOS by Stuehr et al. Stoichiometry experiments demonstrated that during the enzymatic synthesis of 1 mole each of L-citrulline and NO, 2 moles each of NADPH and O2 were consumed with L-arginine as substrate. On the other hand, the oxidation of L-NOHA to citrulline and NO required 1 mole each of NADPH and O2. These results are quite different than those previously reported for macrophage NOS, where the oxidation from L-arginine to L-NOHA requires 1.5 moles of NADPH (Stuehr et al.).

$N^G$-Methyl- and $N^G$-nitro-L-arginine are typical competitive inhibitors for mammalian NOSs. In some cases L-NMA showed irreversible inactivation with macrophage NOSs. Olken, N. M., et al. (1991), Biochem. Biophys. Res. Commun. 177, pp. 828, 833. Both L-NMA and L-NNA appear to be reversible competitive inhibitors for $NOS_{Noc}$ in the presence of either L-arginine or L-NOHA as substrate. this result confirms L-NOHA as an intermediate in the pathway from L-arginine to L-citrulline and NO. Interestingly, the Ki of L-NNA is higher than that of L-NMA with $NOS_{Noc}$. In mammals, the Ki of L-NNA is usually equal or lower than that for L-NMA. Mayer, B., et al. (1993) FEBS Lett. 333, pp. 203–206.

Different stoichiometric relations among products formed and cofactors utilized, differences in Ki measurements, the uniqueness of the measured N-terminal amino acid sequence, and the differences in the molecular weight between $NOS_{Noc}$ and mammalian NOSs all underline possible differences in substrate and cofactor binding to the enzyme active site, and in the catalytic mechanisms involved in the conversion of L-arginine to L-citrulline and NO. $NOS_{Noc}$ may be involved in mechanisms of infection and microbial virulence. $NOS_{Noc}$ is the first NOS to be found in the microbial world. Following the pattern of discovery of other important mammalian enzyme systems in microorganisms such as cytochrome P450s, it is likely that other microbial NOS systems with properties resembling other mammalian NOSs will be discovered. It will therefore be possible to exploit the apparent differences observed here between microbial and mammalian NOSs as the basis for identifying selective NOS inhibitors for possible use and intervention in ineffective diseases.

It can therefore be seen that the above invention accomplishes at least all of its stated objectives.

What is claimed is:

1. A substantially pure and isolated bacterial nitric oxide synthase having the N-terminal amino acid sequence of SEQ ID NO:1.

2. A substantially pure and isolated bacterial nitric oxide synthase according to claim 1 wherein the nitric oxide synthase is isolated from a bacterial species of *Nocardia*.

3. A substantially pure and isolated bacterial nitric oxide synthase according to claim 1 wherein the nitric oxide synthase is a homodimeric protein.

4. A substantially pure and isolated bacterial nitric oxide synthase according to claim 1 wherein the nitric oxide synthase has a denatured molecular weight of about 51,900.

5. A substantially pure and isolated bacterial nitric oxide synthase, purified 1,362-fold in comparison to crude extract and having a molecular weight as a homodimer of approximately 100.6±0.5 kDa by gel filtration.

6. A substantially pure and isolated bacterial nitric oxide synthase according to claim 1 wherein the bacterial nitric oxide synthase has a specific activity of about 203 nmole of NO per mg of protein per min.

\* \* \* \* \*